United States Patent [19]

Freitag

[11] 4,151,913
[45] * May 1, 1979

[54] RETAINING AND INVENTORY PAD FOR SURGICAL SHARPS AND NEEDLES

[75] Inventor: Samuel L. Freitag, Oakland, Calif.

[73] Assignee: Acura-Med, San Leandro, Calif.

[*] Notice: The portion of the term of this patent subsequent to Feb. 22, 1994, has been disclaimed.

[21] Appl. No.: 847,904

[22] Filed: Nov. 2, 1977

[51] Int. Cl.² ............................................. A61L 17/02
[52] U.S. Cl. .................................. 206/370; 206/63.3; 206/382; 206/495
[58] Field of Search .................... 206/63.3, 339, 363, 206/370, 372–373, 382, 459–460, 495, 523; 211/60 R, 60 T; 248/205 R, 205 A

[56] References Cited

U.S. PATENT DOCUMENTS

| | | | |
|---|---|---|---|
| 948,645 | 2/1910 | Boye | 206/382 |
| 3,819,039 | 6/1974 | Erickson | 248/205 A X |
| 3,944,069 | 3/1976 | Eldridge, Jr. | 206/63.3 X |
| 3,951,263 | 4/1976 | Vale | 206/382 |
| 4,008,802 | 2/1977 | Freitag | 206/460 X |

Primary Examiner—William Price
Assistant Examiner—Joseph M. Moy
Attorney, Agent, or Firm—Julian Caplan

[57] ABSTRACT

An improvement on U.S. Pat. No. 4,008,802 wherein a raised, preferably integral, strip of resilient material is provided into the exposed edge of which surgical sharps may be inserted. Transverse printed lines divide the raised strip into sharp receiving zones which are consecutively numbered. Needle receiving zones such as those disclosed in U.S. Pat. No. 4,008,802 may be provided in other areas of a pad, the needle zones being preferably numbered in a separate sequence from the sharp receiving zones. The pad, when it has performed its function may be folded over and held in such position by VELCRO fastener material.

2 Claims, 3 Drawing Figures

RETAINING AND INVENTORY PAD FOR SURGICAL SHARPS AND NEEDLES

This invention is a new and useful improvement in retaining and inventory pad for surgical sharps and needles and is an improvement of U.S. Pat. No. 4,008,802. Many of the objects and advantages of the invention disclosed in said U.S. Pat. No. 4,008,802 are also present in this invention.

Prior U.S. Pat. No. 4,008,802 disclosed a pad used in surgery having ridges and transverse lines dividing the pad into needle receiving zones which were consecutively numbered. The ridges facilitated inserting the surgical needles in a position such that they were secure and visible. By inserting the needles sequentially in the numbered zones, it is possible at a glance to count the number of needles placed on the pad and by comparing the count with the number of needles dispensed at the beginning of the operation, danger of needles being lost is greatly reduced with a consequent reduction in possibility of injury to the patient or operating personnel and of malpractice.

The present invention, in addition to accommodating surgical needles, is provided with a raised area into which surgical "sharps" or the blades of scalpels may be inserted sequentially in numbered zones. Thus the invention not only facilitates counting needles but also sharps. Danger of loss or misplacement of sharps is another hazard to patients and operating personnel and a source of malpractice.

A principal feature of the invention is the provision of a raised ridge, preferably along one side of the pad having an inward directed edge into which the cutting point or edge of a surgical sharp may easily be inserted. The reinforcing material on the back of the pad prevents the sharp from penetrating through the device.

When the operation has been completed and the count of the needles and sharps has been made and compared with the quantity of each dispensed at the beginning of the operation, the pad is folded over, thereby concealing the needles and sharps and preventing them from injuring personnel, whereupon the pad may be discarded.

Other objects of the present invention will become apparent upon reading the following specification and referring to the accompanying drawings in which similar characters of reference represent corresponding parts in each of the several views.

Figure 1:
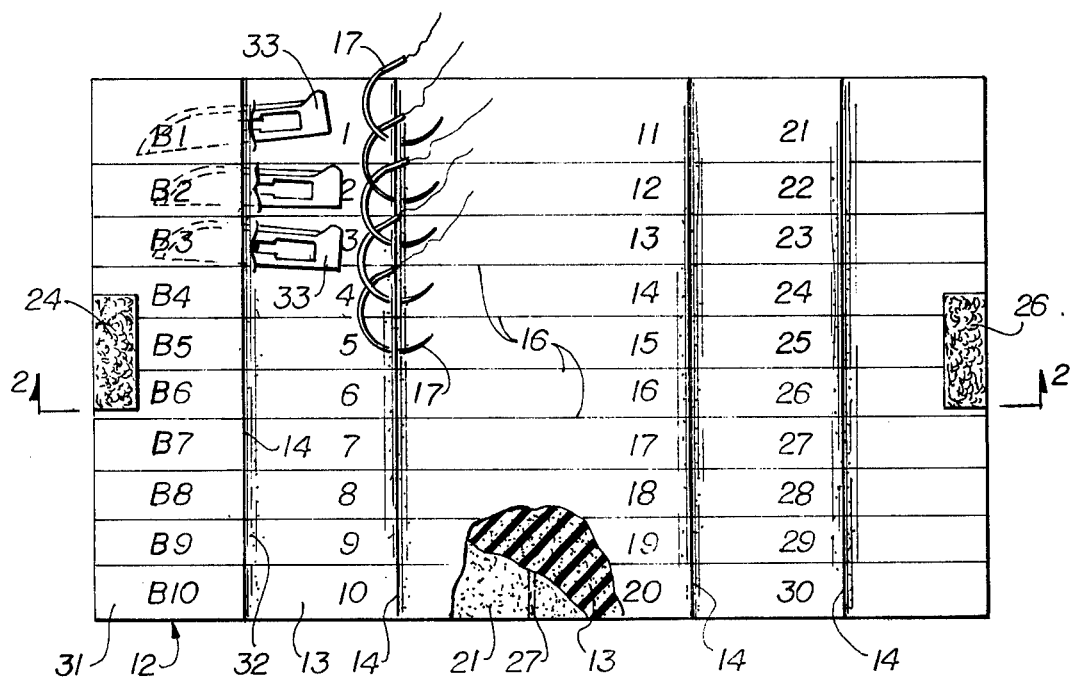
FIG. 1 is a top plan view of a pad in accordance with the present invention.

Pad 12 is desirably of rectangular shape and comprises a base sheet 13 having spaced apart, desirably parallel ridges 14 projecting upwardly from the upper face of the sheet. Extending transversely at right angles across the upper face of the sheet and the ridges are spaced apart parallel lines 16 formed of printing ink which, together with the ridges, divide the pad into a plurality of side-by-side rows or of needle receiving zones indicated by reference letter Z. The zones are marked consecutively with numbers 1 through the total number of needle receiving zones, here shown to be 30.

Each row of zones, there being three zones in the preferred embodiment, contains ten zones numbered consecutively in each row. The lines 16 and the zone numbers are marked on the top face of the pad by any suitable printing means. Each ridge 14 is desirably continuous but it provides a portion thereof adjacent each zone Z into which a surgical needle 17 may be laterally inserted by means of the usual implement, such as a needle holder (not shown); and after being inserted, is firmly retained in the ridge.

During surgery, when a needle is removed from a patient, the nurse or surgeon, using a needle holder, inserts the needle in one of the ridges, the first needle being inserted in the needle zone marked 1 and each subsequent needle being inserted into a consecutive zone. Such procedure is continued until all the needles removed from the patient are placed or received on the pad. An accurate count of needles is thus readily made rapidly and is easily verified.

Pad 12 and the ridges 14 thereon are preferably integrally formed either by molding or by cutting of a soft elastomeric material, such as polyurethane foam.

In a preferred embodiment, to reinforce the pad, the back surface is adhesively bonded to a relatively stiff but flexible backing sheet 21, desirably 4-ply paperboard. On the back surface of the backing sheet 21 are strips 22 of pressure-sensitive tape which are normally covered with release paper 23. When the pad is to be used in surgery, the strips 23 are removed and the pressure-sensitive strips 22 provide means for adhesively holding the pad to a support in the surgery room, such as a surgical drape.

Figure 3:
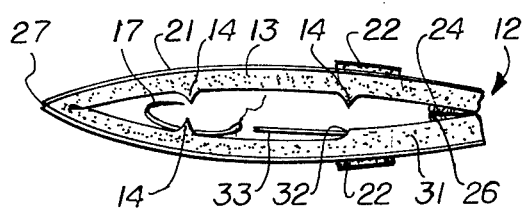
FIG. 3 is an end elevation with the pad folded over in condition for disposal.
Figure 2:
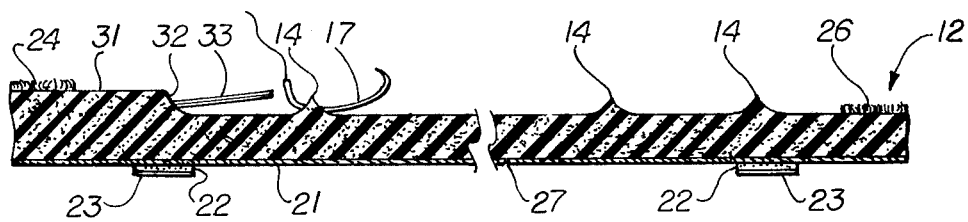
FIG. 2 is an enlarged sectional view, partly broken away to conserve space taken substantially along the line 2—2 of FIG. 1.

Means is provided after surgery to enable the pad to be folded on itself, thereby covering the needles (and sharps hereinafter described) so that personnel is not injured by contact therewith. For such purpose, opposite edges of the pad 12 are provided with fastening material, a preferred fastener being a type known commercially as VELCRO, the hook-like portion 14 being attached on one edge and the felt-like portion 16 being attached directly opposite on the opposite edge. When the pad 12 is folded upon itself, as shown in FIG. 3, the fastener materials 14, 16 adhere, holding the pad together and thus rendering the pad completely disposable with the used needle 17 and the sharps 33, hereinafter described, completely encased. To facilitate folding, backing sheet 21 is peferably provided with a line of weakness 27 such as a perforation line.

The foregoing description is similar to that in U.S. Pat. No. 4,008,802 except that in the foregoing description and in the accompanying drawings there are three rather than four ridges and the fastening means is Velcro material rather than the pressure-sensitive material disclosed in the foregoing patent.

Accurate count and safe disposal of surgical "sharps" is another problem which comprises a hazard to patients and personnel. In accordance with the present invention, along the left edge of FIG. 1 is a raised strip 31 of the same material as the pad 13 having an exposed inner edge 32 along its inward side edge. Sharps 33 are thin, extremely sharp blades provided with means for attachment to a handle (not shown). When the sharps 33 are disengaged from the handle, their pointed ends are pushed into the edge 32 and under the raised portion 31. The backing material 21 prevents the points from extending entirely through the pad. The sharp receiving zones are numbered consecutively B1 . . . B10 in the accompanying drawing and divided one from the other by the same transverse lines 16 which divide the needle receiving zones 1–30. It will be understood that, if desired, the spacing between the sharp receiving zones may be greater or less than that between the needle receiving zones and that the line 16 need not be continuous. Separate numbering B1–B10 may be employed or other satisfactory numerical designations may be used.

The insertion of the sharps in the sharp receiving zones enables a rapid count of the number of sharps which have been used and removed from the area of the incision to be made.

What is claimed is:

1. An improved surgical needle and sharp retaining and inventory pad comprising a base sheet having at least one row of consecutively numbered needle receiving zones on a first face thereof and a separate row of consecutively numbered sharp receiving zones on said first face, a continuous ridge of resilient flexible material projecting upright from said first face adjacent each needle zone into which a surgical needle can be inserted and retained, said ridge being integral with said base sheet, and a relatively stiff backing sheet adhered to a second face of said base sheet opposite said first face, said needle zones being defined by said ridge and by lines on said first face extending transversely of said ridge, wherein the improvement comprises a substantially rectangular raised strip of said flexible material projecting up from said first face and integral with said base sheet, said raised strip having an inward facing edge substantially normal to said first face, said strip being divided into said sharp receiving zones by lines on said strip, said base being formed of flexible polyurethane foam-like material, said ridge in cross-section being triangular and said strip in cross-section being rectangular.

2. A pad according to claim 1 in which said retaining means comprises cooperating separately constructed bits of VELCRO materials on opposite edges of said first face.

* * * * *